US006362354B1

(12) United States Patent
Bunel et al.

(10) Patent No.: US 6,362,354 B1
(45) Date of Patent: Mar. 26, 2002

(54) PHOSPHONITE LIGANDS, CATALYST COMPOSITIONS AND HYDROFORMYLATION PROCESS UTILIZING SAME

(75) Inventors: Emilio Enrique Bunel; Kathryn E. Schwiebert, both of Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/715,967

(22) Filed: Nov. 17, 2000

(51) Int. Cl.[7] .................. C07F 17/02; B01J 31/00; C07C 45/00

(52) U.S. Cl. .................. 556/14; 568/451; 502/155; 556/19; 556/136; 556/138

(58) Field of Search .................. 556/13, 14, 19, 556/136, 138, 156; 502/155; 568/451

(56) References Cited

U.S. PATENT DOCUMENTS

| | | |
|---|---|---|
| 3,907,847 A | 9/1975 | Keblys |
| 4,769,498 A | 9/1988 | Billig et al. |
| 5,028,734 A | 7/1991 | Drent |
| 5,210,260 A | 5/1993 | Bohshar et al. |
| 5,250,726 A | 10/1993 | Burke |
| 5,288,903 A | 2/1994 | Bunel et al. |
| 5,312,996 A | 5/1994 | Packett |
| 5,523,453 A | 6/1996 | Breikss |
| 5,710,344 A | 1/1998 | Breikss et al. |
| 5,817,850 A | 10/1998 | Pastor et al. |
| 5,817,883 A | 10/1998 | Briggs et al. |
| 5,821,378 A | 10/1998 | Foo et al. |
| 5,821,389 A | 10/1998 | Briggs et al. |
| 5,886,237 A | 3/1999 | Packett et al. |
| 5,892,127 A | 4/1999 | Packett et al. |

FOREIGN PATENT DOCUMENTS

| | | |
|---|---|---|
| DE | 195 32 394 | 2/1995 |
| EP | 0 033 554 | 8/1981 |
| EP | 0 872 469 | 10/1998 |
| EP | 0 872 483 | 10/1998 |

OTHER PUBLICATIONS

Tetrahedron Letters by Laly et al pp1183–1185 Feb. 2000.*
CA:74:112174 abs of J Organometallic Chem. by Bishop et al 27(2) pp 241–9.*
Von Bernhard Fell und Walter Boll, Kobaltcarbonyl– und Rhodiumcarbonyl–Katalysatorsysteme bei der Hydroformylierung von 1,3–Dienen, Chemiker–Zeitung, 99, Jahrgang (1975), Nr. 11, pp. 452–458.

(List continued on next page.)

Primary Examiner—Jean F. Vollano

(57) ABSTRACT

Phosphonite ligands, catalyst compositions containing such ligands and a hydroformylation process using such catalyst compositions involving a bidentate phosphonite ligand having the structure represented by the following

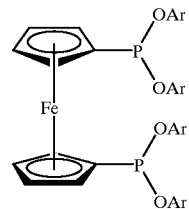

wherein the Ar groups are either the same or different unbridged organic aromatic groups such as substituted or unsubstituted phenyl, substituted or unsubstituted naphthyl, mixtures thereof or the like are disclosed. The ligands in combination with a Group VIII metal or Group VIII metal compound are particularly useful in a hydroformylation process for reacting an ethylenically unsaturated compound to produce linear alkenals at high selectivity.

21 Claims, 1 Drawing Sheet

OTHER PUBLICATIONS

Von Bernhard Fell, Walter Boll und Jens Hagen, Reaktionsprodukte der Hydroformylierung konjugierter Diene mit Rhodiumcarbonyl/tert. Phosphin–Katalysatorsystemen, Chemiker–Zeitung, 99, Jahrgang (1975), Nr. 12, pp. 485–492.

Bernhard Fell and Helmut Bahrmann, The Hydroformylation of Conjugated Dienes, V* Aliphatic Tertiary Phosphines and P–Substituted Phospholanes As Cocatalysts of the Rhodium–Catalysed Hydroformylation of 1,3–Dienes, Journal of Molecular Catalysis, 2 (1977), pp. 211–218.

P.W.N.M. Van Leeuwen and C.F. Roobeek, The Hydroformylation of Butadiene Catalysed By Rhodium–Diphosphine Complexes, Journal of Molecular Catalysis, 31 (1985), pp. 345–353.

Yugi Ohgomori, Naoki Suzuki, Naoko Sumitani, Formatin of 1,6–hexanedial via hydroformylation of 1,3–butadiene, Journal of Molecular Catalysis A: Chemical 133 (1998), pp. 289–291.

Bernhard Fell und Peter Hermanns, Hydroformylierung von Buta–1,3–dien und butadienhaltigen Kohlenwasserstoffraktionen nach dem Zweiphasenverfahren, Two–phase Hydroformylation of Buta–1,3–diene and Hydrocarbon Mixtures Containing Buta–1,3–diene, J. prakt. Chem. 340 (1998), pp. 459–467.

Yoshihiro Sato, Toyoki Nishimata, and Miwako Mori, Novel Synthesis of Heterocycles Using Nickel(O)–Catalyze [2+2+2] Cocyclization: Catalytic Asymmetric Synthesis of Iosindoline and Isoquinoline Derivatives, Heterocycles, vol. 44, No. 1, 1997, pp. 443–457.

Hiroki Yoshizaki, Hisao Satoh, Yoshihiro Sato, Seiji Nukui, Masakatsu Shibasaki, and Miwako Mori, Palladium–Mediated Asymmetric Synthesis of Cis–3,6–Disubstituted Cyclohexenes. A Short Total Synthesis of Optically Active (+)––Lycorane, J. Org. Chem., 1995, 60, pp. 2016–2021.

Barry M. Trost and Michel Spagnol, Nickel catalysed coupling of allylamines and boronic acids, J. Chem. Soc. Perkin Trans. 1, 1995, pp. 2083–2096.

Manfred T. Reetz, Andreas Gosberg, Richard Goddard and Suk–Hun Kyung, Diphosphonites as highly efficient ligands for enantioselective rhodium–catalyzed hydrogenation, Chem. Commun., 1998, pp. 2077–2078.

J.J. Bishop, A. Davidson, M.L. Katcher, D.W. Lichtenberg, R.E. Merrill and J.C. Smart, Symmetrically Disubstituted Ferrocenes, I. The Synthesis of Potential Bidentate Ligands, Journal of Organometallic Chemistry, 27 (1971) pp. 241–249.

Homer R. Yeh, Formation fo Sulfoxide 'Dimers' From Hydrogen Peroxide Oxidation of 2–Chloroethyl Methyl Sulfide and 2–Chloroethyl Ethyl Sulfide, Phosphorus, Sulfur, and Silicon, 1992, vol. 68, pp. 1–7.

T. Jongsma, P. Kimkes and G. Challa, A new type of highly active polymer–bound rhodium hydroformylation catalyst, Polymer, 1992, vol. 33, No. 1, pp. 161–165.

R.R. Holmes and J.A. Forstner, Tetraphosphorus Hexamethylhexaimide [2,4,6,8,9,10–Hexamethyl–2,4,6,8,9,10–hexaaza–1,3,5,7–tetraphosphaadamantane; Phosphorus(III) Methylimide], Inorganic Syntheses, vol. 8 (1966), pp. 63–68.

J. Gloede, B. Costisella und H. Gross, Derivatives of o–Phenylene Phosphate.34.Halogenation of o–Methoxyphenyl Phosphinites, Phosphonites, and Phosphites, Z. anorg. allg. Chem. 535 (1986), pp. 221–228.

O.J. Scherer u. R. Thalacker, Chlorodimethylphosphite–synthesis and some Reactions, Z. Naturforsch, 27b, [1972], pp. 1429–1430.

Gregory D. Cuny and Stephen L. Buchwald, Practical, High–Yield, Regioselective, Rhodium–Catalyzed Hydroformylation of Functionalized a–Olefins, J. Am. Chem. Soc. 1993, 115, pp. 2066–2068.

* cited by examiner

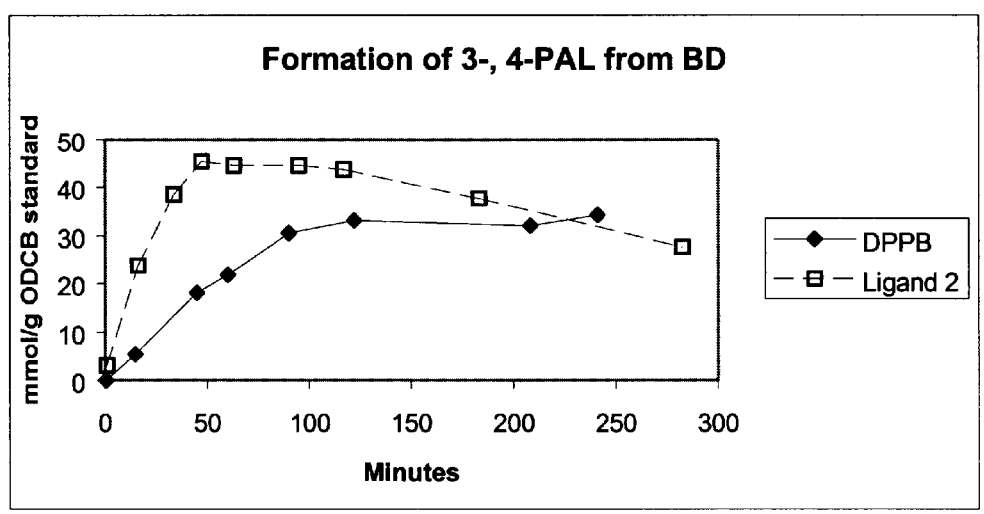
FIGURE

PHOSPHONITE LIGANDS, CATALYST COMPOSITIONS AND HYDROFORMYLATION PROCESS UTILIZING SAME

CROSS-REFERENCE TO RELATED APPLICATIONS

"Not Applicable"

STATEMENT REGARDING FEDERALLY SPONSORED RESEARCH OR DEVELOPMENT

"Not Applicable"

BACKGROUND OF THE INVENTION

1. Field of the Invention

This invention relates to the use of certain ferrocene bisphosphonite ligands in the presence of a Group VIII metal to catalyze the hydroformylation of $C_4$ to $C_{20}$ conjugated dienes to alkenals. The invention also relates to composition of selected hydroformylation catalysts derived from phosphonite ligands and a Group VIII metal. The invention further relates to the composition of the phosphonite ligands.

2. Description of the Related Art

The hydroformylation of alkadienes to produce alkenals, for example the hydroformylation of butadiene to pentenals, is generally known. Pentenals are potential intermediates to a variety of useful compounds. Pentenals may be oxidized and optionally esterified to pentenoic acids or methyl pentenoates, which in turn can be hydroformylated to 5-formylvaleric acid or 5-formylvalerates. 5-Formylvaleric acid and 5-formylvalerates are useful intermediates in the production of epsilon caprolactam. Currently processes for the direct production of pentenoic acids or methyl pentenoates by carbonylation of butadiene may require high temperatures; i.e., greater than 120° C. An advantage of hydroformylation of butadiene to pentenals is that it requires much lower temperatures; i.e., less than 100° C.

Most processes to produce pentenoic acid or pentenoate esters involve the use of halide promoted catalysts such as described in U.S. Pat. Nos. 5,250,726 and 5,288,903. These processes have the disadvantage that they use high concentrations of hydrohalogenic acids and other rigorous conditions, which necessitate cost-increasing measures in connection with safety and the corrosion of the equipment. In U.S. Pat. No. 5,028,734 issued Jul. 2, 1991, a process is described for the selective carbonylation of a conjugate diene by contacting with carbon monoxide in the presence of a hydroxyl group-containing compound such as methanol. This catalyst system is less corrosive than the process that is described in U.S. Pat. Nos. 5,250,726 and 5,288,903 but still has the disadvantage of requiring the use of a catalyst consisting of palladium, a bidentate phosphine and an acid to catalyze the transformation of butadiene to pentenoate esters. The main disadvantage of the presence of an acid is its reactivity towards the alcohol and the bidentate phosphines used in the process. Alcohols will react with the acid promoter to produce esters and phosphines will be converted to phosphonium salts. The combination of these two factors renders the invention described in U.S. Pat. No. 5,028,734 non-practical from an industrial point of view.

Pentenals may be alternatively hydrogenated to pentenols, which upon hydroformylation give hydroxyhexanals. 6-Hydroxyhexanal is a useful intermediate in the production of epsilon caprolactone.

Pentenals may be alternatively hydroformylated to dialdehydes, including adipaldehyde. Adipaldehyde is a valuable intermediate which is potentially useful in the production of compounds such as adipic acid (by oxidation), hexamethylenediamine (by reductive amination), and 1,6-hexanediol (by hydrogenation). Production of adipaldehyde by hydroformylation of pentenals would be a desirable improvement over current processes based on the oxidation of cyclohexane because it is based on butadiene, a less expensive feedstock.

Although a variety of complexes of bis(phosphorus) ligands with rhodium catalyze the hydroformylation of butadiene, the selectivity for 3- and 4-pentenals is low for many of them. Various publications in the 1970's and 1980's, describe hydroformylation of butadiene catalyzed by rhodium complexes with monodentate phosphines (For example, Fell, B. and W. Rupilius *Tetrahedron Lett.* 1969, 2721–3; Fell, B. and W. Boll *Chem.-Ztg.* 1975, 99, 452–8; Fell, B., W. Boll, and J. Hagen *Chem.-Ztg.* 1975, 99, 485–92; Fell, B. and H. Bahrmann *J. Mol. Catal.* 1977, 2, 211–18). These systems yield primarily valeraldehyde because the rhodium/phosphine catalysts are also very efficient catalysts for hydrogenation. Van Leeuwen reported that under mild conditions (95° C. and 175 psi, (1.2 MPa), 1:1 $H_2/CO$) rhodium complexes of bidentate phosphines also yield primarily valeraldehyde (European Patent No. EP33554 A2, Van Leeuwen, P. W. N. M. and C. F. Roobeek *J Mol. Catal.* 1985, 31, 345–53). Recently, however, Ohgomori reported that under more vigorous conditions (100° C. and 1300 psi, (8.9 MPa), 1:1 $H_2/CO$) these catalysts give 3-and 4-pentenals (Ohgomori, Y., Suzuki, N., and Sumitani, N. *J. Mol. Catal.* 1998, 133, 289–291). However, under these conditions the pentenals undergo further hydroformylation to a mixture of dialdehydes, lowering the yield. It has also been reported that hydroformylation of butadiene under biphasic conditions using the sulfonated phosphine $P(C_6H_4\text{-}3\text{-}SO_3Na)_3$ yields 3-pentenal (B. Fell, P. Hermanns, and H. Bahrmann, *J. Parrot. Chem.*, 340 (1998), pp. 459–467, German Patent No. DE 19532394).

A recent series of patents (U.S. Pat. No. 5,312,996, U.S. Pat. No. 5,817,883, U.S. Pat. No. 5,821,389, European Patent No. 872,469, European Patent No. 872,483, U.S. Pat. Nos. 5,892,127, 5,886,237, and European Patent No.872,483) discloses a hydroformylation process in which rhodium complexes of bidentate phosphite ligands catalyze the hydroformylation of butadiene to 3-pentenals. U.S. Pat. No. 5,710,344 discloses the use of rhodium complexes of bidentate phosphorus ligands wherein the ligand contains a bridging group bonded through P—O bonds to a pair of trivalent phosphorus atoms with the other two bonds to each phosphorus being either a pair of P—N bonds (phosphorodiaminites), a pair of P—C bonds (phosphinites) or one P—N and one P—C bond (phosphoroaminites).

These prior art processes using rhodium complexes of bidentate phosphorus ligands to produce 3-pentenal from butadiene have various disadvantages. For example, the isolation of 3-pentenal in these systems is complicated by side reactions such as isomerization to 2-pentenal, reduction to valeraldehyde, and further hydroformylation to a mixture of dialdehydes. Thus, these catalysts do not give high selectivity to 3-pentenal at high conversions of butadiene. For example, the highest selectivity reported for a rhodium complex of a bis(phosphite) ligand is 84% at 37% conversion of butadiene (U.S. Pat. No. 5,886,237). The bis (phosphinite) ligands disclosed in U.S. Pat. No. 5,710,344 disclose up to 95% selectivity at 95% conversion of butadiene, but only in the presence of greater than 5 equivalents of the bis(phosphinite) ligand.

Although bidentate phosphonite ligands are not commonly used in catalysis, they have been employed as catalysts for a variety of transformations, including nickel-catalyzed cyclotrimerization of alkynes (*Heterocycles*, 1997, 44, 443–457), nickel- and palladium-catalyzed alkylations and cross couplings (*J. Org. Chem.* 1995. 60, 2016–2; *J Chem. Soc., Perkin Trans.* 1, 1995, 17, 2083–96), nickel-catalyzed hydrocyanation of olefins (U.S. Pat. No. 5,523,453), and rhodium-catalyzed enantioselective hydrogenation of olefins (Reetz, M., Gosberg, A., Goddard, R., Kyung, S.-H.. *Chem. Commun.* 1998, 19, 2077–2078).

Bidentate phosphonite ligands based on a ferrocene backbone have been disclosed in U.S. Pat. No. 5,817,850 (see Fig. A below) and *Chem. Commun.* 1998, 19, 2077–2078. The bidentate phosphonites described in these publications have biphenol or binaphthol derived terminal groups that are bridged. U.S. Pat. No. 5,817,850 discloses a hydrocarbonylation reaction of an alkene with carbon monoxide and hydrogen to form an aldehyde which is catalyzed by a transition metal complex of the bridged terminal group containing ferrocene bis(phosphonite) disclosed therein.

FIG. A

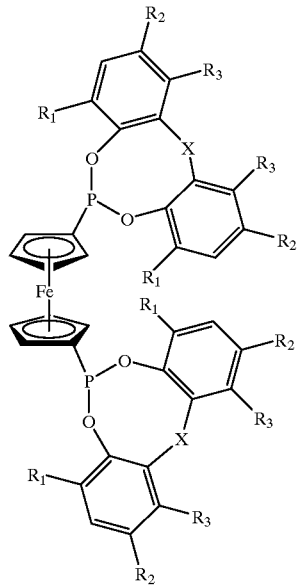

(X is alkylidene, S, Se, or a direct bond)

Furthermore, while the catalyst systems described above may represent commercially viable catalysts, it always remains desirable to provide even more effective, higher performing catalyst precursor compositions, catalytic compositions and catalytic processes to achieve full commercial potential for a desired reaction. The improvement in effectiveness and/or performance may be achieved in any or all of rapidity, selectivity, efficiency or stability.

The successful hydroformylation of conjugated dienes and/or selectivity for linear aldehyde products are particularly desirable attributes.

BRIEF SUMMARY OF THE INVENTION

The invention provides for a bidentate phosphonite ligand having the structure represented by the following Formula I:

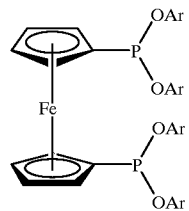

Formula I wherein the Ar groups are either the same or different unbridged organic aromatic groups such as substituted or unsubstituted phenyl, substituted or unsubstituted naphthyl, mixtures thereof or the like. It should be appreciated that for purposes of this invention the above structural formula is illustrative of the staggered configuration of phosphonite ferrocene; i.e., $(\eta^5\text{-}C_5H_4P(OAr)_2)Fe$, but is not intended to be limiting. As such the eclipsed configuration as well as rotational variations thereof are to be considered intrinsically equivalent to the illustrated staggered configuration as generally known in the art.

The present invention further provides for a hydroformylation process comprising the steps of reacting an ethylenically unsaturated compound with CO and $H_2$ in the presence of a catalyst composition comprising a Group VIII metal or Group VIII metal compound and phosphonite ligand having a structure represented by Formula I and thus producing an aldehyde. The invention is especially directed to a hydroformylation process involving the reaction of a conjugated $C_4$ to $C_{20}$ diene with CO and $H_2$ in the presence of the catalyst composition.

The invention also provides for certain bidentate phosphonite ligands and catalyst compositions made therefrom useful in hydroformylation processes. In particular, these include the combination of a ligand of Formula I with a suitable Group VIII metal or Group VIII metal catalyst precursor.

BRIEF DESCRIPTION OF THE DRAWING

The FIGURE is a plot of the cumulative millimoles of 3- and 4-pentenals (PAL) produced by the hydroformylation of butadiene (BD) per gram of internal GC standard, ortho-dichlorobenzene (ODCB), as a function of time using rhodium complexed with a di(2-t-butylphenylphosphonite) ferrocene ligand (Ligand 2) according to the instant invention compared to using bis(diphenylphosphinic) butane (DPPB) as the rhodium-complexing ligand.

DETAILED DESCRIPTION OF THE INVENTION

The catalyst compositions useful in the processes of the invention are comprised of certain bidentate phosphonite ligands and a transition metal.

The phosphonite ligands described in Formula I may be prepared by a variety of methods known in the art. 1,1'-Dilithioferrocene can be prepared according to *J. Organomet. Chem.*, 1971, 27(2). 241-0, 1,1-Bis (dichlorophosphino)ferrocene can be prepared from 1,1,'-dilithioferrocene according to *Phosphorus, Sulfur Silicon Relat. Elem.*, 1992, 68(1–4), 99–106 or *Chem. Commun.* (*Cambridge*), 1998, 19, 2077–2078. Ligands of Formula I can be prepared by contacting 1,1'-bis(dichlorophosphino) ferrocene with four or more equivalents of a substituted or unsubstituted phenol. *Chem. Commun.* (*Cambridge*), 1998, 19, 2077–2078 describes the related reaction of 1,1'-bis (dichlorophosphino)ferrocene with (R)-binaphthol at temperatures greater than 25° C. We have found, however, that in the presence of a base such as triethylamine, this reaction can be carried out at room temperature.

Alternatively, phosphonite ligands described in Formula I may be prepared by contacting 1,1'-dilithioferrocene with a phosphorochlorodite of Formula II.

Formula II wherein the Ar groups are unbridged and can be any substituted or unsubstituted phenyl, naphthyl, or other aromatic constituent.

Phosphorochloridites may be prepared by a variety of methods known in the art, for example, see descriptions in Polymer, 1992, 33, 161; *Inorganic Synthesis,* 1966, 8, 68; U.S. Pat. No. 5,210,260; *Z. Anorg. Allg. Chem.,* 1986, 535,221. With ortho-substituted phenols, phosphorochloridites can be prepared in situ from $PCl_3$ and the phenol. Also, phosphorochloridites of 1-naphthols can be prepared in situ from $PCl_3$ and 1-naphthols in the presence of a base like triethylamine. Another process for preparing the phosphorochlorodite comprises treatment of N,N-dialkyl diarylphosphoramidite with HCl. $ClP(OMe)_2$ has been prepared in this manner, see *Z. Naturforsch,* 1972, 27B, 1429. Phosphorochloridites derived from substituted phenols have been prepared using this procedure as described in commonly assigned U.S. Pat. No. 5,821,378.

By contacting the thus obtained $(OAr)_2PCl$ with 1,1'-dilithioferrocene, for example by the method described in U.S. Pat. No. 5,817,850, a bidentate phosphonite ligand according to the invention is obtained which also can be used in the process according to the invention.

The transition metal of hydroformylation catalyst system may be any transition metal capable of carrying out catalytic reaction and may additionally contain labile ligands, which are either displaced during the catalytic reaction or take an active part in the catalytic transformation. Any of the transition metals may be considered in this regard. The preferred metals are those comprising Group VIII of the Periodic Table. The preferred metals for hydroformylation are rhodium, cobalt, iridium, ruthenium, palladium and platinum, and rhodium is especially preferred.

Group VIII compounds suitable for hydroformylation, can be prepared or generated according to techniques well known in the art, as described, for example, WO 95 30680, U.S. Pat. No. 3,907,847, and *J. Amer. Chem. Soc.,* 1993, 115, 2066. Examples of suitable Group VIII metals are ruthenium, rhodium, and iridium. Suitable Group VIII metal compounds are hydrides, halides, organic acid salts, acetylacetonates, inorganic acid salts, oxides, carbonyl compounds and amine compounds of these metals. Examples of suitable Group VIII metal compounds are, for example, $Ru_3(CO)_{12}$, $Ru(NO_3)_2$, $RuCl_3(Ph_3P)_3$, $Ru(acac)_3$, $Ir_4(CO)_{12}$, $IrSO_4$, $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$ (wherein "acac" is an acetylacetonate group; "OAc" is an acetyl group; "COD" is 1,5-cyclooctadiene; and "Ph" is a phenyl group). However, it should be noted that the Group VIII metal compounds are not necessarily limited to the above listed compounds. The Group VIII metal is preferably rhodium. Rhodium compounds that contain ligands that can be displaced by the multidentate phosphites are a preferred source of rhodium. Examples of such preferred rhodium compounds are $Rh(CO)_2$ (acetylacetonate), $Rh(CO)_2$ $(tC_4H_9COCHCO-tC_4H_9)$, $Rh_2O_3$, $Rh_4(CO)_{12}$, $Rh_6(CO)_{16}$, $Rh(O_2CCH_3)_2$, and Rh(2-ethylhexanoate). Rhodium supported on carbon may also be used in this respect.; i.e., as the source of rhodium.

The present invention also provides a process for hydroformylation, comprising reacting an ethylenically unsaturated compound with a source of CO and $H_2$ in the presence of a catalyst precursor composition comprising a transition metal selected from the group of Co, Rh, Ru, Ir, Pd, and Pt, and at least one bidentate phosphonite ligand selected from the group represented by Formula I as described above.

The olefinically unsaturated starting materials useful in this invention include unsaturated organic compounds containing at least one carbon to carbon double bond, "C=C", and preferably from 2 to 20 carbon atoms. Examples of suitable olefinically unsaturated organic compounds are linear terminal olefinic hydrocarbons, for example, ethylene, propylene, 1-butene, 1-pentene, and higher hydrocarbons; branched terminal olefins, for example isobutene and 2-methyl-1-butene; linear internal olefinic hydrocarbons, for example, cis- and trans-2-butene, cis- and trans-2-hexene, and cis- and trans-3-hexene; branched internal olefinic hydrocarbons, for example, 2,3-dimethyl-2-butene, 2-methyl-2-butene and 2-methyl-2-pentene; terminal olefinic hydrocarbon-internal olefinic hydrocarbon mixtures; for example, octenes prepared by dimerization of butenes; olefin oligomer isomer mixture from butadiene, dimer to tetramer of lower butadiene olefins including propylene, n-butene, isobutene or the like; and cycloaliphatic olefinic hydrocarbons, for example, cyclopentene, cyclohexene, 1-methylcyclohexene, cyclooctene, and limonene. The olefinically unsaturated compounds can be substituted with one or more functional groups containing a heteroatom, such as oxygen, sulfur, nitrogen, or phosphorus. Examples of these heteroatom-substituted olefinically unsaturated organic compounds include vinyl methyl ether, methyl oleate, oleyl alcohol, allyl alcohol, methyl 2-pentenoate, methyl 3-pentenoate, methyl 4-pentenoate, 3-pentenoic acid, 4-pentenoic acid, 3-pentenenitrile, 4-pentenenitrile, 7-octen-1-al, acrylonitrile, acrylic acid esters, methyl acrylate, methacrylic acid esters, methyl methacrylate, acrolein and other substituted olefinically unsaturated compounds. Other examples of suitable olefinic compounds include those substituted with an unsaturated hydrocarbon group including olefinic compounds containing an aromatic substituent such as styrene, α-methylstyrene, and allyl benzene; and diene compounds such as 1,3-butadiene, 1,5-hexadiene, 1,7-octadiene, and norbornadiene.

The invention is especially directed to hydroformylation processes in which a linear olefinically unsaturated aldehyde is prepared starting from a conjugated diene. The hydroformylation of $C_4$ to $C_{20}$ conjugated dienes to alkenals is especially preferred, for example, the hydroformylation of butadiene to pentenal.

It is a significant advantage of the invention that concentration of the olefinically unsaturated starting materials in the reactor may be increased. The normal undesirable side effects of such an increase, for example, the formation of oligomer and/or the inhibition of the catalyst, are avoided. Solvent recycle may be reduced or eliminated with its attendant benefits. Thus, in a preferred embodiment of the invention, the olefinically unsaturated starting material (i.e., the reactant involved in the hydroformylation reaction) is advantageously present in the liquid phase reaction media at a concentration of at least 40 weight percent.

The hydroformylation process according to the invention can be performed as described below:

The reaction conditions of the hydroformylation process according to this invention are in general the same as used in a conventional process, described, for example, in U.S. Pat. No. 4,769,498, which is incorporated herein by reference, and will be dependent on the particular starting ethylenically unsaturated organic compound. For example, the temperature can be from room temperature to 200° C., preferably from 50 to 120° C. The pressure may vary from atmospheric pressure to 20 MPa, preferably from 3 to 20 MPa for conjugated dienes such as 1,3-butadiene. The pressure is preferably equal to the combined hydrogen and carbon monoxide partial pressures. Extra inert gases may however be present. The molar ratio of hydrogen to carbon monoxide is generally between 10 to 1 and 1 to 10, preferably between 6 to 1 and most preferably 1 to 2.

The amount of Group VIII metal compound is not specially limited, but is optionally selected so that favorable results can be obtained with respect to catalyst activity and economy. In general, the concentration of Group VIII metal in the reaction media is between 10 and 10,000 ppm and more preferably between 50–500 ppm, calculated as the free metal.

The molar ratio of multidentate phosphorus ligand to Group VIII metal is not specially limited, but is optionally selected so that favorable results can be obtained with respect to catalyst activity, aldehyde selectivity, and process economy. This ratio generally is from about 0.5 to 100 and preferably from 1 to 5 (moles of ligand to moles of metal). Most preferably, the molar ratio of bidentate phosphonite ligand of Formula I to rhodium metal is selected to be equal to or slightly greater than the stoichiometric equivalent of one mole of ligand to one mole of metal.

The hydroformylation reaction of the instant invention can be performed in the presence of a solvent. The choice of solvent is not critical provided the solvent is not detrimental to catalyst, reactant and product. The solvent may be a mixture of reactants, such as the starting unsaturated compound, the aldehyde product and/or by-products. Suitable solvents include saturated hydrocarbons such as kerosene, mineral oil or cyclohexane, ethers such as diphenyl ether, tetrahydrofuran or a polyglycol, ketones such as methyl ethyl ketone and cyclohexanone, nitriles such as acetonitrile, valeronitrile, and benzonitrile, aromatics such as toluene, benzene and xylene, esters such as dimethylformamide, and sulfones such as tetramethylenesulfone.

The following examples are presented to more fully demonstrate and further illustrate various individual aspects and features of the present invention and the showings are intended to further illustrate the differences and advantages of the present invention. As such, the examples are felt to be non-limiting and are meant to illustrate the invention but are not meant to be unduly limiting.

EXAMPLE 1

Synthesis of Ligand I

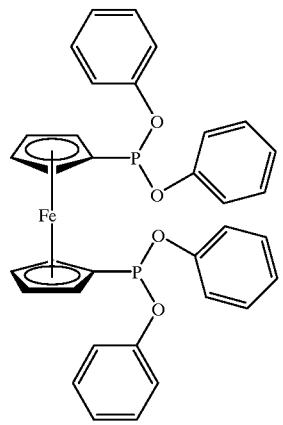

All manipulations were carried out in a drybox under an atmosphere of nitrogen. To a cold (−35° C.) suspension of diphenyl phosphorochloridite (0.30 g, 1.2 mmol) in diethyl ether (20 mL) was added a cold (−35° C,) suspension of the TMEDA (tetramethylethylenediamine) complex of dilithioferrocene (0.17 g, 0.4 mmol) in diethyl ether (5 mL). This mixture was allowed to stand at −35° C. for several days. The reaction was allowed to warm to room temperature. The solution was filtered through neutral alumina, and the solvent was removed to give 0.18 g of an orange solid. $^{31}$P NMR ($d_8$-toluene): δ161.6, with a second peak at δ129.1.

EXAMPLE 1A

Hydroformylation of Butadiene using Ligand 1

A solution containing Rh(acac)(CO)$_2$ (0.040 g), Ligand 1 (0.13 g), 1,3-butadiene (4.6 g) and 1,2-dichlorobenzene (1.1 g, GC internal standard) in 50 mL of toluene was prepared in a drybox. This solution was loaded into a 100 mL autoclave under a stream of H$_2$/CO. The autoclave was charged to 100 psig (0.69 MPa) with 1:1 H$_2$/CO and heated to 95° C. Once the temperature had stabilized, the pressure was adjusted to 1000 psig (6.9 MPa). The mixture was stirred at approximately 900 rpm with an air-driven rotary stirrer for 1 hour. Samples were withdrawn via a needle valve and analyzed by gas chromatography on an Hewlett Packard (Palo Alto, Calif.) 5890A Chromatograph with a fused silica capillary column (Model DB5, 30 meters, 0.32 mm I.D., 0.25 μm film thickness) purchased from J & W Scientific (Folsom, Calif.). GC analysis after 30 minutes indicated conversion of butadiene: 51%; selectivity to 3- and 4-pentenals: 87% on a mole basis. GC analysis after 60 minutes indicated conversion of butadiene: 79%; selectivity to 3- and 4-pentenals: 79% on a mole basis.

EXAMPLE 2

Synthesis of Ligand 2

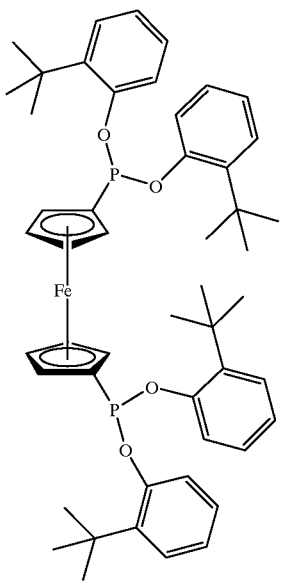

A cold (−35° C.) solution of di-2-t-butylphenyl phosphorochloridite (7.6 g, 20.9 mmol) in 100 mL of toluene was added to a cold (−35° C.) suspension of the TMEDA complex of dilithioferrocene (3 g, 0.7 mmol) in 200 mL of toluene. This mixture was allowed to stand at −35° C. for one hour. The reaction was allowed to warm to room temperature and stirring continued for 18 hours. The solution was filtered through celite, and the solvent was removed under vacuum. Pentane (100 ml) was added to precipitate 2.2 g of Ligand 2 as an orange solid. $^{31}$P NMR (CD$_2$Cl$_2$): δ163.

EXAMPLE 2A

Hydroformylation of Butadiene using Ligand 2

A solution containing Rh(acac)(CO)$_2$ (0.044 g), Ligand 2 (0.16 g), 1,3-butadiene (4.3 g) and 1,2-dichlorobenzene (1.1 g, GC internal standard) in 50 mL of toluene was prepared in a drybox. This solution was loaded into a 100 mL autoclave under a stream of H$_2$/CO. The autoclave was charged to 100 psig (0.69 MPa) with 1:1 H$_2$/CO and heated to 95° C. Once the temperature had stabilized, the pressure was adjusted to 1000 psig (6.9 MPa). The mixture was stirred at approximately 900 rpm with an air-driven rotary stirrer for 45 minutes. Samples were withdrawn via a needle valve and analyzed by gas chromatography on an Hewlett Packard 5890A Chromatograph with a fused silica capillary column (Model DB5, 30 meters, 0.32 mm I.D., 0.25 μm film thickness) purchased from J & W Scientific. GC analysis after 45 minutes indicated conversion of butadiene: 89%; selectivity to 3- and 4-pentenals: 81% on a mole basis.

EXAMPLE 3

Synthesis of Ligand 3

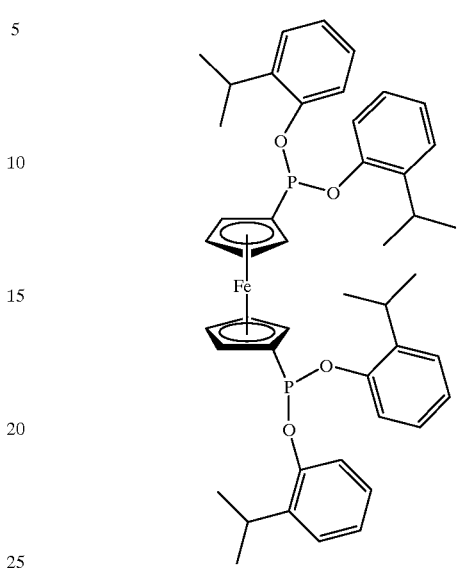

A solution containing triethylamine (0.68 g, 6.7 mmol) and 2-isopropylphenol (0.91 g, 6.7 mmol) in 10 mL of toluene was slowly added into a solution containing 1,1'-bis(dichlorophosphino)ferrocene (0.52 g, 1.4 mmol) in 30 mL of toluene. This mixture was allowed to stir at 25° C. for 60 hours. The solution was filtered through celite and neutral alumina. The solvent was removed under vacuum to yield Ligand 3 as an orange oil. $^{31}$P NMR (CD$_2$Cl$_2$): δ162.5.

EXAMPLE 3A

Hydroformylation of Butadiene using Ligand 3

A solution containing Rh(acac)(CO)$_2$ (0.031 g), Ligand 3 (0.31 g), 1,3-butadiene (3.7 g) and 1,2-dichlorobenzene (0.8 g, GC internal standard) in 38 mL of toluene was prepared in a drybox. This solution was loaded into a 100 mL autoclave under a stream of H$_2$/CO. The autoclave was charged to 100 psig (0.69 MPa) with 1:1H$_2$/CO and heated to 95° C. Once the temperature had stabilized, the pressure was adjusted to 1000 psig (6.9 MPa). The mixture was stirred at approximately 900 rpm with an air-driven rotary stirrer for 45 minutes. Samples were withdrawn via a needle valve and analyzed by gas chromatography on an Hewlett Packard 5890A Chromatograph with a fused silica capillary column (Model DB5, 30 meters, 0.32 mm I.D., 0.25 μm film thickness) purchased from J & W Scientific. GC analysis after 30 minutes indicated conversion of butadiene: 71%; selectivity to 3- and 4-pentenals: 85% on a mole basis. GC analysis after 45 minutes indicated conversion of butadiene: 89%; selectivity to 3- and 4-pentenals: 77% on a mole basis.

EXAMPLE 4

Synthesis of Ligand 4

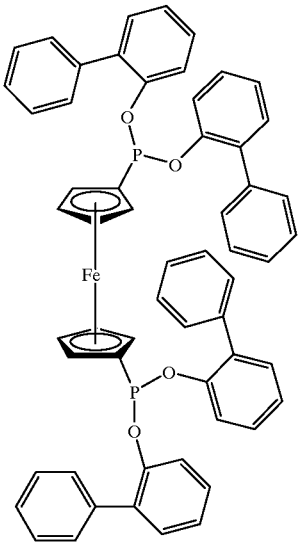

A solution containing triethylamine (0.56 g, 5.5 mmol) and 2-phenylphenol (0.95 g, 5.6 mmol) in 10 mL of toluene was slowly added into a solution containing 1,1'-bis(dichlorophosphino)ferrocene (0.48 g, 1.2 mmol) in 25 mL of toluene. This mixture was allowed to stir at 25° C. for 18 hours. The solution was filtered through celite. The solvent was removed under vacuum to yield Ligand 4 as an orange solid. $^{31}$P NMR (CD$_2$Cl$_2$): δ162.

EXAMPLE 4A

Hydroformylation of Butadiene using Ligand 4

A solution containing Rh(acac)(CO)$_2$ (0.044 g), Ligand 4 (0.28 g), 1,3-butadiene (4.3 g) and 1,2-dichlorobenzene (1.1 g, GC internal standard) in 50 mL of toluene was prepared in a drybox. This solution was loaded into a 100 mL autoclave under a stream of H$_2$/CO. The autoclave was charged to 100 psig (0.69 MPa) with 1:1 H$_2$/CO and heated to 95° C. Once the temperature had stabilized, the pressure was adjusted to 1000 psig (6.9 MPa). The mixture was stirred at approximately 900 rpm with an air-driven rotary stirrer for 45 minutes. Samples were withdrawn via a needle valve and analyzed by gas chromatography on an Hewlett Packard 5890A Chromatograph with a fused silica capillary column (Model DB5, 30 meters, 0.32 mm I.D., 0.25 μm film thickness) purchased from J & W Scientific. GC analysis after 30 minutes indicated conversion of butadiene: 84%; selectivity to 3- and 4-pentenals: 84% on a mole basis. GC analysis after 45 minutes indicated conversion of butadiene: 95%; selectivity to 3- and 4-pentenals: 76% on a mole basis.

EXAMPLE 5

Synthesis of Ligand 5

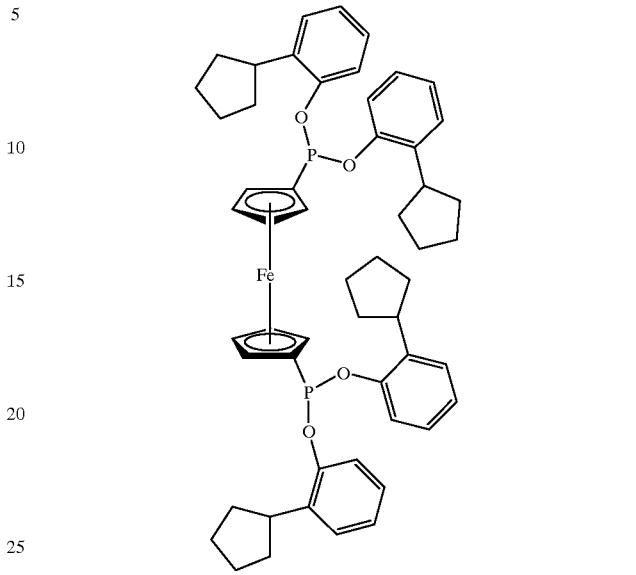

A solution of 2-cyclopentylphenol (1.01 g, 6.3 mmol) in 10 mL of toluene was slowly added into a solution of 1,1'-bis(dichlorophosphino) ferrocene (0.54 g, 1.4 mmol) in 20 mL of toluene. Triethylamine (0.58 g, 5.7 mmol) was added and the mixture was allowed to stir at 25° C. for 60 hours. The solution was filtered through celite and neutral alumina. The solvent was removed under vacuum to yield Ligand 5 as an orange oil. $^{31}$P NMR (CD$_2$Cl$_2$): δ163.

EXAMPLE 5A

Hydroformylation of Butadiene using Ligand 5

A solution containing Rh(acac)(CO)2 (0.043 g), Ligand 5 (0.19 g), 1,3-butadiene (5.1 g) and 1,2-dichlorobenzene (1.0 g, GC internal standard) in 50 mL of toluene was prepared in a drybox. This solution was loaded into a 100 mL autoclave under a stream of H$_2$/CO. The autoclave was charged to 100 psig (0.69 MPa) with 1:1 H$_2$/CO and heated to 95° C. Once the temperature had stabilized, the pressure was adjusted to 1000 psig (6.9 MPa). The mixture was stirred at approximately 900 rpm with an air-driven rotary stirrer for 45 minutes. Samples were withdrawn via a needle valve and analyzed by gas chromatography on an Hewlett Packard 5890A Chromatograph with a fused silica capillary column (Model DB5, 30 meters, 0.32 mm I.D., 0.25 μm film thickness) purchased from J & W Scientific. GC analysis after 30 minutes indicated conversion of butadiene: 66%; selectivity to 3- and 4-pentenals: 77% on a mole basis. GC analysis after 45 minutes indicated conversion of butadiene: 83%; selectivity to 3- and 4-pentenals: 76% on a mole basis.

EXAMPLE 6

Synthesis of Ligand 6

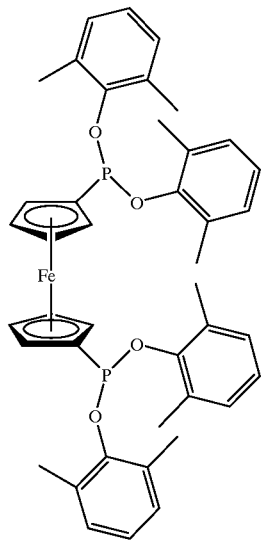

A solution containing triethylamine (0.68 g, 6.7 mmol) and 2,5-dimethylphenol (0.85 g, 7 mmol) in 10 mL of toluene was slowly added into a solution containing 1,1'-bis(dichlorophosphino)ferrocene (0.63 g, 1.6 mmol) in 25 mL of toluene. This mixture was allowed to stir at 25° C. for 18 hours. The solution was filtered through celite and the solvent was removed under vacuum. The residue was dissolved in toluene and filtered through celite and neutral alumina. Toluene was removed under vacuum to yield Ligand 6 as an orange solid. $^{31}$P NMR (CD$_2$Cl$_2$): δ163.

EXAMPLE 6A
Hydroformylation of Butadiene using Ligand 6

A solution containing Rh(acac)(CO)$_2$ (0.043 g), Ligand 6 (0.25 g), 1,3-butadiene (4.3 g) and 1,2-dichlorobenzene (1.1 g, GC internal standard) in 50 mL of toluene was prepared in a drybox. This solution was loaded into a 100 mL autoclave under a stream of H$_2$/CO. The autoclave was charged to 100 psig (0.69 MPa) with 1:1 H$_2$/CO and heated to 95° C. Once the temperature had stabilized, the pressure was adjusted to 1000 psig (6.9 MPa). The mixture was stirred at approximately 900 rpm with an air-driven rotary stirrer for 240 minutes. Samples were withdrawn via a needle valve and analyzed by gas chromatography on an Hewlett Packard 5890A Chromatograph with a fused silica capillary column (Model DB5, 30 meters, 0.32 mm I.D., 0.25 μm film thickness) purchased from J & W Scientific. GC analysis after 150 minutes indicated conversion of butadiene: 74%; selectivity to 3- and 4-pentenals: 82% on a mole basis. GC analysis after 45 minutes indicated conversion of butadiene: 78%; selectivity to 3- and 4-pentenals: 73% on a mole basis.

EXAMPLE 6B
Hydroformylation of Butadiene using Ligand 6

A solution containing Rh(acac)(CO)$_2$ (0.086 g), Ligand 6 (0.58 g) and 1,2-dichlorobenzene (2.1 g, GC internal standard) in 56.7 grams of toluene was prepared in a drybox. This solution was loaded into a 100 mL autoclave under a stream of H$_2$/CO. The autoclave was charged to 100 psig (0.69 MPa) with 1:1 H$_2$/CO, 41 mL of butadiene were then added with a syringe pump and heated to 95° C. Once the temperature had stabilized, the pressure was adjusted to 930 psig (6.4 MPa). The mixture was stirred at approximately 900 rpm with an air-driven rotary stirrer for 240 minutes. Samples were withdrawn via needle valve and analyzed by gas chromatography on an Hewlett Packard 5890A Chromatograph with a DB5 fused silica capillary column (30 meters, 0.32 mm I.D., 0.25 μm film thickness) purchased from J & W Scientific. GC analysis after 30 minutes indicated conversion of butadiene: 53.5%; selectivity to 3- and 4-pentenals: 98.5% on a mole basis. GC analysis after 120 minutes indicated conversion of butadiene: 85%; selectivity to 3- and 4-pentenals: 90% on a mole basis.

EXAMPLE 7

Synthesis of Ligand 7

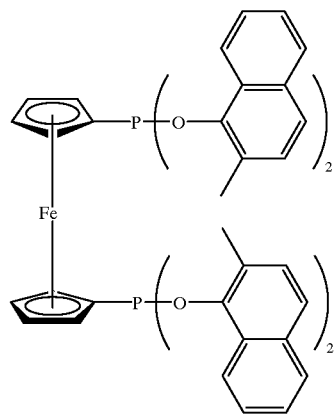

A solution containing triethylamine (0.63 g, 6.2 mmol) and 2-methyl-1-naphthol (1.0 g, 6.3 mmol) in 10 mL of toluene was slowly added into a solution containing 1,1'-bis(dichlorophosphino) ferrocene (0.60 g, 1.5 mmol) in 20 mL of toluene. This mixture was allowed to stir at 25° C. for 18 hours. The solution was filtered through celite and neutral alumina. The solvent was removed under vacuum to yield Ligand 7 as an orange oil. 31P NMR (CD$_2$Cl$_2$): δ164.

EXAMPLE 7A
Hydroformylation of Butadiene using Ligand 7

A 29.3 gram portion of a solution containing Rh(acac)(CO)$_2$ (0.086 g), Ligand 7 (0.7 g) in 58 grams of toluene was combined with 1,2-dichlorobenzene (0.5 g, GC internal standard). This solution was loaded into a 100 mL autoclave under a stream of H$_2$/CO. The autoclave was charged to 100 psig (0.69 MPa) with 1:1 H$_2$/CO, 12.1 mL of butadiene were then added with a syringe pump and heated to 95° C. Once the temperature had stabilized, the pressure was adjusted to 930 psig (6.4 MPa). The mixture was stirred at approximately 900 rpm with an air-driven rotary stirrer for 240 minutes. Samples were withdrawn via needle valve and analyzed by gas chromatography on an Hewlett Packard 5890A Chromatograph with a fused silica capillary column (Model DB5, 30 meters, 0.32 mm I.D., 0.25 μm film thickness) purchased from J & W Scientific. GC analysis after 30 minutes indicated conversion of butadiene: 59%; selectivity to 3- and 4-pentenals: 94.6% on a mole basis. GC analysis after 90 minutes indicated conversion of butadiene: 84.9%; selectivity to 3- and 4-pentenals: 84% on a mole basis.

COMPARATIVE EXAMPLE 8

A solution containing Rh(acac)(CO)$_2$ (0.041 g), bis(diphenyl-phosphino)butane (0.064 g DPPB), 1,3-butadiene (4.0 g BD) and 1,2-dichlorobenzene (1.0 g ODCB, GC internal standard) in 47 mL of toluene was prepared in a drybox. This solution was loaded into a 100 mL autoclave under a stream of $H_2/CO$. The autoclave was charged to 100 psig (0.69 MPa) with 1:1 $H_2/CO$ and heated to 95° C. Once the temperature had stabilized, the pressure was adjusted to 1000 psig (6.9 MPa). The mixture was stirred at approximately 900 rpm with an air-driven rotary stirrer for several hours. Samples were withdrawn via a needle valve and analyzed by gas chromatography on an Hewlett Packard 5890A Chromatograph with a fused silica capillary column (Model DB5, 30 meters, 0.32 mm I.D., 0.25 μm film thickness) purchased from J & W Scientific. GC analysis after 63 minutes indicated conversion of butadiene: 70%; selectivity to 3- and 4-pentenals: 86% on a mole basis.

The data from the above procedure are plotted in the FIGURE along with the data for Ligand 2 from Example 2A. The comparative results show the advantage of the phosphonite ligands (e.g. Ligand 2) over the phosphinite ligands of the prior art (e.g., bis(diphenylphosphino)butane; Ohgomori, et al., *N. J. Mol. Catal.* 1998, 133, 289–291). The phosphonite reaches a higher overall conversion to the desired products (3- and 4-pentenals) in a shorter time.

Having thus described and exemplified the invention with a certain degree of particularity, it should be appreciated that the following claims are not to be so limited but are to be afforded a scope commensurate with the wording of each element of the claim and equivalents thereof.

We claim:

1. A phosphonite ligand having the following structure:

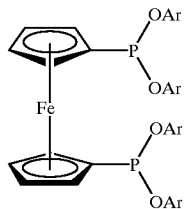

wherein the Ar groups are either the same or different unbridged organic aromatic groups.

2. A phosphonite ligand of claim 1 wherein Ar is selected from the group consisting of substituted or unsubstituted phenyl, substituted or unsubstituted naphthyl, and mixtures thereof.

3. A phosphonite ligand of claim 1 wherein —OAr is selected from the group consisting of:

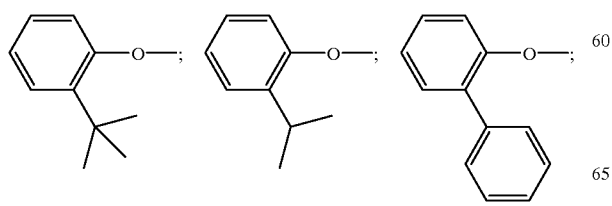

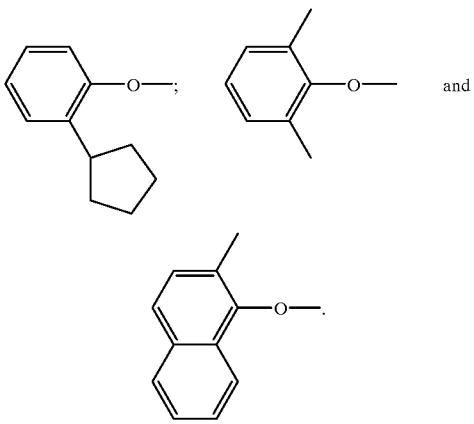

4. A hydroformylation catalyst composition comprising a Group VIII metal or Group VIII metal compound and phosphonite ligand having the following structure:

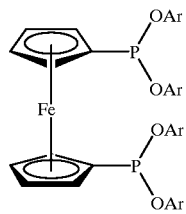

wherein the Ar groups are either the same or different unbridged organic aromatic groups.

5. A phosphonite ligand of claim 4 wherein Ar is selected from the group consisting of substituted of unsubstituted phenyl, substituted or unsubstituted naphthyl, and combinations thereof.

6. A phosphonite ligand of claim 4 wherein —OAr is selected from the group consisting of:

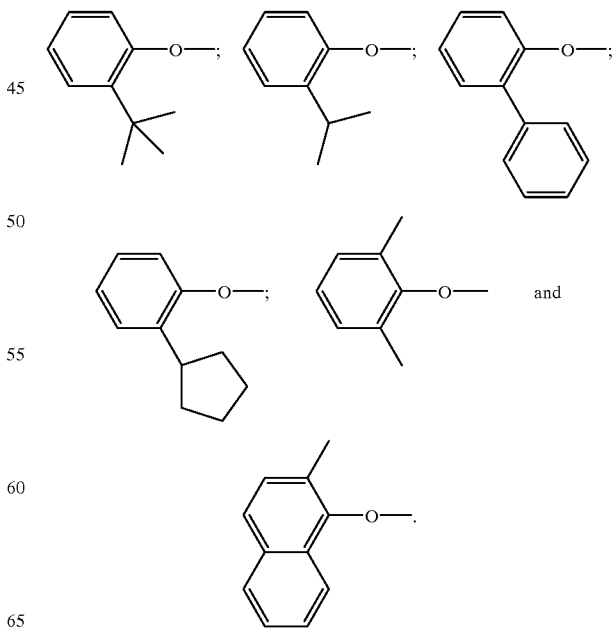

7. A catalyst composition according to claim 4 wherein said Group VIII metal is rhodium, cobalt, iridium, ruthenium, palladium or platinum.

8. A catalyst composition according to claim 4 wherein said Group VIII metal is rhodium.

9. A catalyst composition according to claim 4 wherein said Group VIII metal compound is selected from the group consisting of $RU_3(CO)_{12}$, $Ru(NO_3)_2$, $RuCl_3(Ph_3P)_3$, $Ru(acac)_3$, $Ir_4(CO)_{12}$, $IrSO_4$, $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$ and $[RhCl(COD)]_2$.

10. A catalyst composition according to claim 4 wherein said Group VIII metal compound is selected from the group consisting of $Rh(CO)_2$ (acetylacetonate), $Rh(CO)_2$ ($tC_4H_9COCHCO$—$tC_4H_9$), $Rh_2O_3$, $Rh_4(CO)_{12}$, $Rh_6(CO)_{16}$, $Rh(O_2CCH_3)_2$, and Rh(2-ethylhexanoate).

11. A hydroformylation process comprising the steps of: reacting an ethylenically unsaturated compound with CO and $H_2$ in the presence of a catalyst composition comprising a Group VIII metal or Group VIII metal compound and phosphonite ligand having the following structure:

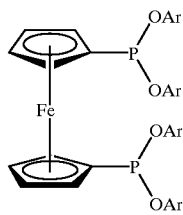

wherein the Ar groups are either the same or different unbridged organic aromatic groups; and producing an aldehyde.

12. A hydroformylation process according to claim 11 wherein Ar is selected from the group consisting of substituted or unsubstituted phenyl, substituted or unsubstituted naphthyl, and combinations thereof.

13. A hydroformylation process according to claim 11 wherein —OAr is selected from the group consisting of:

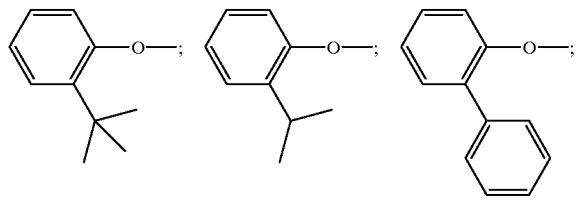

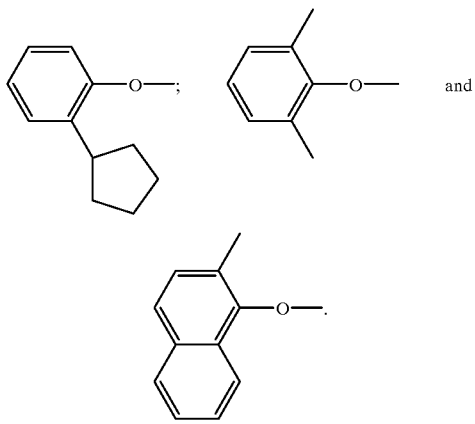

14. A hydroformylation process according to claim 11 wherein said ethylenically unsaturated compound is a conjugated $C_4$ to $C_{20}$ diene.

15. The process of claim 11 wherein the reactants are in the liquid phase.

16. The process of claim 11 wherein the ethylenically unsaturated compound is butadiene.

17. The process of claim 11 wherein the Group VIII metal is rhodium.

18. The process of claim 11 wherein the conversion of butadiene is at least 75 per cent.

19. The process of claim 11 wherein the selectivity to linear aldehydes is at least 80 per cent.

20. The process of claim 13 wherein the concentration of the ethylenically unsaturated compound is at least 40 weight per cent of liquid phase reaction media.

21. A catalyst composition according to claim 8 wherein the rhodium metal is supported on carbon.

* * * * *

UNITED STATES PATENT AND TRADEMARK OFFICE
CERTIFICATE OF CORRECTION

PATENT NO.   : 6,362,354 B1
DATED        : March 26, 2002
INVENTOR(S)  : Bunel et al.

It is certified that error appears in the above-identified patent and that said Letters Patent is hereby corrected as shown below:

Column 9,
Line 61, delete the word "Hewleft" and insert -- Hewlett --.

Column 13,
Line 28, delete "2,5" and insert -- 2,6 --.

Column 14,
Line 42, delete "31" and insert -- $^{31}$ --.

Column 16,
Line 36, delete "of" and insert -- or --.

Signed and Sealed this

Twenty-ninth Day of October, 2002

Attest:

JAMES E. ROGAN
Attesting Officer            Director of the United States Patent and Trademark Office